(12) United States Patent
Habash

(10) Patent No.: US 11,998,536 B2
(45) Date of Patent: Jun. 4, 2024

(54) DECREASING EXPRESSION LEVEL OF PROTEASOME SUBUNIT GENES BY TREATING A HUMAN SUBJECT WITH A NITROXIDE

(71) Applicant: Louis Habash, Irvine, CA (US)

(72) Inventor: Louis Habash, Irvine, CA (US)

( * ) Notice: Subject to any disclaimer, the term of this patent is extended or adjusted under 35 U.S.C. 154(b) by 0 days.

(21) Appl. No.: 17/074,228

(22) Filed: Oct. 19, 2020

(65) Prior Publication Data

US 2021/0169863 A1 Jun. 10, 2021

Related U.S. Application Data

(63) Continuation of application No. 15/877,050, filed on Jan. 22, 2018, now Pat. No. 10,828,291.

(51) Int. Cl.
*A61K 31/445* (2006.01)
*A61K 45/06* (2006.01)
*A61P 35/00* (2006.01)

(52) U.S. Cl.
CPC ............ *A61K 31/445* (2013.01); *A61K 45/06* (2013.01); *A61P 35/00* (2018.01)

(58) Field of Classification Search
None
See application file for complete search history.

(56) References Cited

U.S. PATENT DOCUMENTS

2009/0062338 A1* 3/2009 Habash .................... A61P 9/00
514/408
2012/0046314 A1 2/2012 Habash

FOREIGN PATENT DOCUMENTS

WO WO 2004/075884 9/2004
WO WO 2017/007858 A1 6/2016

OTHER PUBLICATIONS

Liu et al (Atherosclerosis 206:199-203, 2009) (Year: 2009).*
Almond et al. "The proteasome: a novel target for cancer chemotherapy." Leukemia 16.4 (2002): 433-443.
Arlt et al. "Increased proteasome subunit protein expression and proteasome activity in colon cancer relate to an enhanced activation of nuclear factor E2-related factor 2 (Nrf2)." Oncogene 28.45 (2009): 3983-3996.
Balch et al. "Adapting proteostasis for disease intervention." Science 319.5865 (2008): 916-919.
Chen et al. "Increased proteasome activity, ubiquitin-conjugating enzymes, and eEF1A translation factor detected in breast cancer tissue." Cancer Research 65.13 (2005): 5599-5606.

Ciechanover, Aaron. "Proteolysis: from the lysosome to ubiquitin and the proteasome." Nature Reviews Molecular Cell Biology 6.1 (2005): 79-86.
Deshaies, Raymond J. "Proteotoxic crisis, the ubiquitin-proteasome system, and cancer therapy." BMC Biology 12.1 (2014): 94-107.
Finley, Daniel. "Recognition and processing of ubiquitin-protein conjugates by the proteasome." Annual review of biochemistry 78 (2009): 477-513.
Glickman et al. "The regulatory particle of the *Saccharomyces cerevisiae* proteasome." Molecular and Cellular Biology 18.6 (1998): 3149-3162.
Maupin-Furlow et al. "Proteasomes from structure to function: perspectives from Archaea." Current Topics in Developmental Biology 75 (2006): 125-169.
Pickart et al. "Proteasomes and their kin: proteases in the machine age." Nature Reviews Molecular Cell Biology 5.3 (2004): 177-187.
Tanaka, Keiji. "The proteasome: overview of structure and functions." Proceedings of the Japan Academy, Series B 85.1 (2009): 12-36.
Verbrugge et al. "Proteasome inhibitors as experimental therapeutics of autoimmune diseases." Arthritis Research & Therapy 17.1 (2015): 17-26.
Vogelstein et al. "Cancer genome landscapes." Science 339.6127 (2013): 1546-1558.
Warner et al. "*Saccharomyces cerevisiae* coordinates accumulation of yeast ribosomal proteins by modulating mRNA splicing, translational initiation, and protein turnover." Molecular and Cellular Biology 5.6 (1985): 1512-1521.
Weaver et al. "Does aneuploidy cause cancer?" Current Opinion in Cell Biology 18.6 (2006): 658-667.
Williams et al. "Aneuploidy affects proliferation and spontaneous immortalization in mammalian cells." Science 322.5902 (2008): 703-709.
Williams et al. "Aneuploidy: cancer's fatal flaw?." Cancer Research 69.13 (2009): 5289-5291.
PCT/ISA/206—Invitation to Pay Additional Search Fees dated Jun. 19, 2019 in PCT/US19/14278, which is related to the present application.
Kakumu et al (Cancer Sci 108:732-743, 2017) (Year: 2017).
Deng et al., "Over-expression of genes and proteins of ubiquitin specific peptidases (USPs) and proteasome subunits (PSs) in breast cancer tissue observed by the methods of RFDD-PCR and proteomics", Breast Cancer Res Treat (Jul. 2007) vol. 104 No 1 pp. 21-30.
NIH National Cancer Institute—Age and Cancer Risk—Posted Apr. 29, 2015 (Online) URL: https://www.cancer.gov/about-cancer/causes-prevention/risk/age.
PCT Search Report—Written Opinion—in related application PCT/US19/14278 International Filing Date Jan. 18, 2019; dated Aug. 27, 2019.

(Continued)

Primary Examiner — Craig D Ricci
(74) Attorney, Agent, or Firm — Knobbe, Martens, Olson & Bear LLP

(57) ABSTRACT

Some embodiments disclosed herein include a method for decreasing gene expression of a gene. The methods can include identifying a human subject over the age of 35 and having an increase expression level of a gene associated with proteasome activity; and administering to the human subject an effective amount of a nitroxide antioxidant, whereby expression level of the gene is decreased.

10 Claims, No Drawings

(56) References Cited

OTHER PUBLICATIONS

Fleenor et al (Aging Cell 11:269-276, 2012) (Year: 2012).
Yang et al (Neuroscience 154:1107-1120, 2008) (Year: 2008).
Pilarsky et al (Neoplasia 6:744-750, 2004) (Year: 2004).
Giriboldi et al (Free Radical Biol and Med 24:913-923, 1998) (Year: 1998).

* cited by examiner

DECREASING EXPRESSION LEVEL OF PROTEASOME SUBUNIT GENES BY TREATING A HUMAN SUBJECT WITH A NITROXIDE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/877,050, filed Jan. 22, 2018. The aforementioned application is incorporated by reference herein in its entirety, and is hereby expressly made a part of this specification.

BACKGROUND

Field

The present disclosure relates generally to the field of modulation of gene expression and more particularly to decreasing expression levels of one or more genes relating to proteasome activity by treating human subjects with a nitroxide.

Description of the Related Art

Genes generally encode biologically functional products. Gene expression describes transcription of gene encoding DNA sequences into complementary DNA (cDNA) and translation of cDNA into the functional products, such as proteins. Many factors, both internal and external, are involved in regulation of gene expression in cells. Such regulation can manifest in an adjustment of gene expression to increase or decrease a number of proteins made.

Proteasomes (also referred to as proteasomes protein complexes) are present in cells. Many proteins act together to form and carryout the functions of the proteasome. These proteins that makeup the proteasome complex are examples of biologically functional products resulting from gene expression.

Proteolysis is a process of degradation of proteins. Intracellular proteolysis is generally mediated by lysosome activity or proteasome activity. Proteasomes interact with, among other intracellular components, ubiquitin tagged proteins marked for degradation, thereby inhibiting toxicity related to protein buildup within the cell. Proteasomes are present in eukaryotic cells at a high concentration and cleave peptides in an ATP/ubiquitin-dependent process in a non-lysosomal pathway Certain conditions, such as cancer, can be associated with (e.g., causes or caused by) rapid and uncontrolled protein formation, and presence of proteins that would otherwise be marked for degradation. In cells associated with the underlying condition, a toxic intracellular environment can be a desired method of treatment for the condition. Thus, inhibition or proteasome activity in such cells is essential for treatment and prevention of certain conditions.

Other diseases and conditions can often be characterized by abnormal expression of one or more genes. Irregularities in gene expression underlie many diseases and conditions. Overexpression or underexpression of a gene or genes often results in dysfunction of downstream actions controlled by the same. Whether the gene is a regulator of cellular function or a vital in a responsive mechanism, modulation of the gene expression is a fundamental directive in addressing the foundational issues associated with many diseases and conditions.

SUMMARY

Some embodiments disclosed herein provide methods for decreasing gene expression. The methods, in some embodiments, include identifying a human subject over the age of 35 and having an increase expression level of a gene associated with proteasome activity; and administering to the human subject an effective amount of a nitroxide antioxidant resulting in a decreased expression level of the gene. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for decreasing the expression level of a gene in a human subject in need thereof, comprising: identifying a human subject having an increased expression level of a gene associated with proteasome activity; administering to the human subject an effective amount of a nitroxide antioxidant, whereby the expression level of the gene associated with proteasome activity is decreased. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the increased expression level of the gene is age-related. In some embodiments, the human subject is over the age of 35. In some embodiments, the human subject is over the age of 45. In some embodiments, the human subject is over the age of 55. In some embodiments, the human subject is over the age of 65. In some embodiments, the increased expression level of the gene is disease-related. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the disease is age-related. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for reducing risk of a disease in a human subject in need thereof, comprising: identifying a human subject over the age of 35 having an increased risk of a disease due to an increased expression level of a gene associated with proteasome activity; administering to the human subject an effective amount of a nitroxide antioxidant, whereby the expression level of the gene associated with proteasome activity is decreased. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing a cancer and in need of a decreased expression level of a gene associated with proteasome activity; administering to the human subject an effective amount of a nitroxide antioxidant, whereby the expression level of the gene associated with proteasome activity is decreased. In some embodiments, the cancer is associated with (e.g., correlates with) an increased expression level of the gene associated with proteasome activity. The increased expression level of the gene associated with proteasome activity can be a response to rapid cell growth associated with the cancer. Rapid cell growth associated with the cancer may require degradation of ubiquitin-tagged dysfunctional (e.g., improperly folded) proteins. In some embodiments, the cancer can be selected from the group consisting of bladder cancer, colorectal cancer, hepatocellular carcinoma, prostate carcinoma, and kidney carcinoma. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the cancer is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing an autoimmune disease and in need of a decreased expression level of a gene associated with proteasome activity; administering to the human subject an effective amount of a nitroxide antioxidant, wherein the expression level of the gene associated with proteasome activity is decreased. In some embodiments, the autoimmune disease can be selected from the group consisting of rheumatoid/osteoid arthritis, systemic lupus erythematosus (SLE), inflammatory bowel disease, multiple sclerosis, atherosclerosis, and osteoporosis. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the gene is Cd5l. In some embodiments, the autoimmune disease is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for a disease associated with an increased proteasome activity in a patient in need thereof, comprising: identifying a human subject having or at risk of developing a disease associated with an increased expression of a gene associated with proteasome activity; administering to the human subject an effective amount of a nitroxide antioxidant, whereby the expression level of a gene associated with proteasome activity is decreased. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual over the age of 35 in need of an increased expression level of a gene associated with proteasome activity; and administering to the individual an effective amount of a nitroxide antioxidant to decrease the level of expression of the gene associated with proteasome activity. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the human subject is over the age of 45. In some embodiments, the human subject is over the age of 55. In some embodiments, the human subject is over the age of 65. In some embodiments, the human subject has an increased expression level of the gene. In some embodiments, the individual has or is at risk of developing an age-related condition. In some embodiments, the age-related condition comprises increased senescence in a tissue. In some embodiments, the age-related condition comprises hyperactivation of proteasome activity in a tissue. In some embodiments, the age-related condition comprises increased molecular heterogeneity. In some embodiments, the age-related condition comprises increased functional impairment in a tissue. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual having a disease-related increased expression level of a gene associated with proteasome activity; and administering to the individual an effective amount of a nitroxide antioxidant to decrease the level of expression of the gene associated with proteasome activity. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with proteasome activity is decreased. In some embodiments, the individual has an increased expression level of the gene. In some embodiments, the gene is selected from the group consisting of: Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the condition is an age-related condition. In some embodiments, the age-related condition comprises increased senescence in a tissue. In some embodiments, the age-related condition comprises overactivation of proteasome activity in a tissue. In some embodiments, the age-related condition comprises increased molecular heterogeneity. In some embodiments, the age-related condition comprises increased functional impairment in a tissue. In some embodiments, the age-related condition is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the human subject is over the age of 35. In some embodiments, the human subject is over the age of 45. In some embodiments, the human subject is over the age of 55. In some embodiments, the human subject is over the age of 65.

Some embodiments disclosed herein provide methods for decreasing the expression level of a gene in a human subject in need thereof, comprising: identifying a human subject having an increased expression level of a gene associated with proteasome activity, wherein the gene associated with proteasome activity is selected from the group consisting of Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4; and delivering to the human subject an effective amount of a nitroxide antioxidant to reduce the level of expression of the gene associated with proteasome activity. In some embodiments, the nitroxide antioxidant is 4-hydroxy-2,2,6,6-tetramethylpiperidine-1-oxyl. In some embodiments, the increased expression level of the gene is age-related. In some embodiments, wherein the increased expression level of the gene is cancer-related. In some embodiments, the increased expression level of the gene is disease-related. In some embodiments, the increased expression level of the gene is neurodegeneration-related. In some embodiments, the increased expression level of the gene is infection related. In some embodiments, the reduced the level of expression of the gene initiates apoptosis. In some embodiments, the expression level of the gene is reduced in a tissue selected from the group consisting of a skin tissue, an immune tissue, an adipose tissue, a pancreatic tissue, cardiac tissue, and a neuronal tissue by treatment.

Some embodiments disclosed herein provide methods for decreasing an expression level, in an eukaryotic cell, of one or more genes encoding proteins involved in the proteasome complex by contacting the eukaryotic cell with a nitroxide antioxidant. In some embodiments, the one or more genes is selected from the group consisting of Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the nitroxide antioxidant is 4-hydroxy-2,2,6,6-tetramethylpiperidine-1-oxyl. In some embodiments, the eukaryotic cell is a cancer cell. In some embodiments, the expression level of the one or more genes is decreased in said cell in a tissue selected from the group consisting of a skin tissue, an immune tissue, an adipose tissue, a pancreatic tissue, cardiac tissue, and a neuronal tissue. In some embodiments, prior to said contacting, the eukaryotic cell exhibits an age-related increased expression level of said one or more genes. In some embodiments, prior to said contacting, the eukaryotic cell exhibits a disease-related increased expression level of said one or more genes. In some embodiments, prior to said contacting, the eukaryotic cell exhibits a neurodegeneration-related expression level of said one or more genes.

Some embodiments disclosed herein provide methods for improving chemotherapeutic response in a human subject comprising: contacting cancer cells in the subject with an effective amount of a nitroxide antioxidant whereby a level of expression of one or more genes encoding one or more proteasome subunits is decreased in said cancer cells. In some embodiments, said cancer cells are known to have increased proteasome activity. In some embodiments, the decreased expression level of expression of one or more genes following treatment initiates apoptosis within one or more of said cancer cells. In some embodiments, the nitroxide antioxidant is 4-hydroxy-2,2,6,6-tetramethylpiperidine-1-oxyl. In some embodiments, the one or more genes is selected from the group consisting of Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4.

Some embodiments disclosed herein provide methods for reducing proteasome activity in a human subject comprising: identifying a human subject known to have increased proteasome activity; and delivering to the subject an effective amount of a nitroxide antioxidant, whereby a level of expression of a gene encoding one or more proteasome subunits is decreased. In some embodiments, the nitroxide antioxidant is 4-hydroxy-2,2,6,6-tetramethylpiperidine-1-oxyl. In some embodiments, increased proteasome activity is age-related. In some embodiments, the increased proteasome activity is cancer-related. In some embodiments, the increased proteasome activity is disease-related. In some embodiments, the increased proteasome activity is neurodegeneration-related. In some embodiments, the increased proteasome activity is infection-related. In some embodiments, the decreased level of expression of the gene initiates apoptosis. In some embodiments, the expression level of the gene is decreased in a tissue selected from the group consisting of a skin tissue, an immune tissue, an adipose tissue, a pancreatic tissue, cardiac tissue, and a neuronal tissue following treatment.

Some embodiments disclosed herein provide methods for treating a human subject having cancer comprising: delivering an effective amount of a nitroxide antioxidant to a human subject, wherein the human subject has previously been administered at least one chemotherapeutic agent, whereby a level of expression of at least one gene encoding a proteasome is decreased. In some embodiments, the human subject having cancer is identified with an increased expression of one or more genes selected from the group consisting of Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4. In some embodiments, the methods further comprise administering a proteasome inhibitor to the human subject.

DETAILED DESCRIPTION

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, N Y 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "expression" means the a gene product that is expressed or produced by one or more nucleic acid molecules detectable by standard molecular biology methods, which gene product refers to e.g. an unspliced RNA, an mRNA, a splice variant mRNA, a polypeptide, a post-translationally modified polypeptide, a splice variant polypeptide etc., and specifically products made using an RNA gene product as a template, e.g. cDNA of the RNA.

As used herein, "differential expression" of a gene means that the expression of the gene is at a higher level ("increased expression") or lower level ("decreased expression") in a human subject suffering from a disease, for example cancers and autoimmune diseases, relative to its expression in a normal or control subject. Differential expression includes both quantitative, as well as qualitative, differences in the temporal or cellular expression pattern in a gene or its expression products among, for example, normal and diseased cells, or among cells which have undergone different disease events or disease stages.

As used herein, "decreasing the expression level" of a gene means causing the expression of the gene to decrease by treating the human subject with a compound, for example a nitroxide antioxidant, such that the expression level of the gene after treatment is lower than the expression level of the gene before treatment in the human subject.

As used herein, "delivering" a compound means bringing that compound into contact with a relevant cell, tissue, or organism. Similarly, "contacting" means that the compound contacts a relevant target, such as a tissue or cell or tumor. In either case, delivery or contact in an organism can be affected by directly administering the compound to the organism, or by administering a different compound to the organism, such as a prodrug that is converted in vivo to the desired compound. In short, these terms cover any action that leads to contact between the desired compound and a target cell, tissue, or organism.

The present disclosure describes methods of modulating gene expression in human subjects. However, this is illustrative only and not intended to be limiting. For example, the methods disclosed herein can be used for modulating gene expression in other vertebrates, such as but not limited to mammals, birds, reptiles, fish, and the like (with modifications wherein appropriate). Mammals and birds include most agricultural animals. Treatment of companion animals, e.g., dogs, cats, or birds is also contemplated.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Disclosed herein include methods for preventing, ameliorating, or treating one or more conditions in a subject (e.g., a human subject) in need thereof. The one or more conditions can be associated with (e.g., caused by) a disease (e.g., cancer, autoimmune diseases, etc.). The conditions may be associated with (e.g., correlated with) an increased level (e.g., expression level) of proteasome genes. In some embodiments, a nitroxide antioxidant (e.g., 4-hydroxy-2,2, 6,6-tetramethylpiperidine-1-oxyl) is administered to the subject, whereby the expression level of one or more proteasome genes. Administering of the nitroxide antioxidant in the subject can result in a decreased level of one or more proteasome genes. The involvement of a proteasome gene in a particular condition may relate to the ability for the ubiquitin mediated proteasome degradation of the ubiquitin-tagged proteins. For example, in cancer, cells rapidly produce large amounts of dysfunctional proteins that require an increase in proteasome activity to accommodate the degradation of the dysfunctional proteins. This increase may be a result of various mechanisms, including the uncontrolled proliferation of the cells. In some embodiments, a nitroxide antioxidant can be, or act like, a proteasome inhibitor that promotes apoptosis. In some embodiments, decreased expression level of proteasome genes prevents, ameliorates, or treats the one or more conditions.

Human Subject Identification

The present disclosure relates to methods of treating alteration in gene expression, such as age-related, cancer-related, disease-related, neurodegeneration-related, and infection-related alteration in gene expression. Gene expression changes also play important roles in aging and serve as biomarkers of physiological decline and disease conditions, such as neurodegenerative diseases, and cancers. Therefore, one aspect of the present disclosure is methods of treating a human subject having an age-related, cancer-related, disease-related, neurodegeneration related, and/or infection-related increase in gene expression levels, such as those genes associated with proteasome activity. In some embodiments, the human subject can be identified based on the human subject's age, gene expression level, family history, health conditions, medical history, habits, or a combination thereof.

Regardless of the cause of the upregulation, some common terminology can be used. In some embodiments, the expression level of a gene (e.g., a gene associated with proteasome activity) in a human subject is considered to be upregulated or increased if the increase in the expression level of that gene is statistically significant compared to that of a control or a reference. In some embodiments, the expression level of a gene (e.g., a gene associated with proteasome activity) in a human subject is considered to be upregulated or increased if the increase in the expression level of that gene is statistically significant compared to that of a control or a reference. The control or reference can be, for example, a normal healthy population, a population at large, a collection of individuals of the same age or condition or sex, or the same human subject at a different time (e.g., at an earlier time of life when the human subject does or does not have the disease or condition that results in the upregulation).

In some embodiments, a normal healthy population or a population at large can be a population having the same or similar gender, age, and/or race, compared to the human subject. In some embodiments, the expression level of the gene in the control or reference can be the mean or median expression level of the gene in control subjects in the control or reference subjects in the reference. The increase in expression level can be statistically significant if the probability of the observed difference occurring not by chance, the confidence level, is greater than a threshold. The threshold can be, or be about, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values.

In some embodiments, the increase in expression level can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the increase in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

In some embodiments, the human subject may have an age that is, is about, or is over 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years old.

In some embodiments, the human subject is identified based on the human subject's expression profiles of one or more genes associated with proteasome activity. Non-limiting exemplary methods for determining the human subject's expression profiles include: amplification techniques such as PCR and RT-PCR (including quantitative variants), hybridization techniques such as in situ hybridization, microarrays, blots, and others, and high throughput sequencing techniques like Next Generation Sequencing (Illumina, Roche Sequencer, Life Technologies SOLID™), Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Non-limiting exemplary methods for determining the human subject's expression profiles include: binding techniques such as ELISA, immunohistochemistry, microarray and functional techniques such as enzymatic assays.

Genes Associated with Proteasome Activity

In some embodiments, administering to the human subject an effective amount of the nitroxide antioxidant results in an increased expression level of a gene, for example a gene associated with proteasome activity. Therefore, some embodiments disclosed herein provide methods for treating an individual in need thereof, comprising identifying an individual having a disease-related increased expression level of a gene associated with proteasome activity; and administering to the individual an effective amount of a nitroxide antioxidant to decrease the level of expression of the gene associated with proteasome activity. Some embodiments disclosed herein provide methods for treating an individual in need thereof, comprising identifying an individual in need of a decreased expression level of a gene associated with proteasome activity; and administering to the individual an effective amount of a nitroxide antioxidant to decrease the level of expression of the gene associated with proteasome activity. Some embodiments disclosed herein provide methods for treating an individual in need thereof, comprising: administering to the individual, known to have a disease-related increased expression level of a gene associated with proteasome activity, an effective amount of a nitroxide antioxidant to decrease the level of expression of the gene associated with proteasome activity. Some embodiments disclosed herein provide methods for treating an individual in need thereof, comprising: administering to an individual, known to be in need of a decreased expression level of a gene associated with proteasome activity, an effective amount of a nitroxide antioxidant to decrease the level of expression of the gene associated with proteasome activity.

Non-limiting examples of diseases associated with altered level of proteasome activity include cancer; breast cancer; lung cancer; kidney cancer; cancers of the ovary and uterus; cancer of the central nervous system; cancers of the head and neck; melanoma; lymphomas; leukemia; neurological disorders; Alzheimer's disease; Parkinson's disease; Huntington's disease; amyotrophic lateral sclerosis; stroke; cardiovascular disorders; ischemia; heart failure; infections, infectious diseases; bacterial infections; inflammatory responses; viral infections; autoimmune diseases; systemic lupus erythematosus; autoimmune lymphoproliferative syndrome; rheumatoid arthritis; and thyroiditis.

Non-limiting exemplary genes involved in proteasome activity include those classified as Psma1, Psma2, Psma3, Psma4, Psma5, Psma6, Psma7, Psma8, Psme1, Psme2, Psme3, Psme4, Psmf, Psmg1, Psmg2, Psmg3, Psmg4, Shfm1, Pomp, Paaf1, Kiaa0368, Usp14, Hch15, Ube3C, Ube3A, Park2, Rad23A/B, Ubqln1/2; classified as beta-type subunits Psmb1, Psmb2, Psmb3, Psmb4, Psmb5, Psmb6, Psmb7, Psmb8, Psmb9, Psmb10, Psmb11; classified as ATPase subunits Psmc1, Psmc2, Psmc3, Psmc4, Psmc5, Psmc6; classified as non-ATPase subunits Psmd1, Psmd2, Psmd3, Psmd4, Psmd5, Psmd6, Psmd7, Psmd8, Psmd9, Psmd10, Psmd11, Psmd12, Psmd13, Psmd14, Adrm1.

The gene associated with proteasome activity can be Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. For example, the treatment can result in decreased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof. The decreased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof, can decreased the level of proteasome activity. The decreased level of proteasome activity can result in a decrease in or disappearance of signs and symptoms of a disease associated with increased proteasome activity, including the curing of the disease associated with increased proteasome activity. In some embodiments, the increased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof, can decrease the level of proteasome activity. The decreased level of proteasome activity can result in a decrease in or disappearance of signs and symptoms of the disease associated with increased proteasome activity, including the curing of the disease associated with increased proteasome activity. In some embodiments, the decreased level of proteasome activity can inhibit, suppress, prevent, or reverse the disease or the symptoms associated with the disease.

Proteasome

The proteasome is a protein complex comprised of multiple subunits within eukaryotic cells. Functionally, proteasomes are configured to degrade unnecessary or dysfunctional proteins through proteolysis of peptide bonds within the proteins targeted for degradation. In this way, the proteasome regulates intracellular protein concentration generally preventing cytotoxic environments known to trigger apoptosis.

The 26S proteasome, a multicatalytic protease complex over 2.5 MDa, is responsible for degradation of a variety of proteins in cells, and thus helps maintain intracellular protein homeostasis (Ciechanover A. Proteolysis: from the lysosome to ubiquitin and the proteasome. Nat Rev Mol Cell Biol. 2005; 6:79-87; Finley D. Recognition and processing of ubiquitin-protein conjugates by the proteasome. Annu Rev Biochem. 2009; 78:477-513; and Pickart C M, Cohen R E. Proteasomes and their kin: proteases in the machine age. Nat Rev Mol Cell Biol. 2004; 5:177-187; the content of each is incorporated herein by reference in its entirety). In mammals, cytosolic proteasome 26S is generally comprised of three main subunits. Two 19S cap subunits generally define terminal ends of a 20S core subunit wherein proteolysis occurs. Both the cap and core subunits are comprised of further subunits distinguishable by their contribution to the overall proteasome complex. Alpha subunits are generally structural, while beta subunits within the 20S core are catalytic to facilitate proteolysis.

The ubiquitin-proteasome system (UPS) is the major mechanism by which proteins are degraded in the cytoplasm and nucleus of eukaryotic cells and as such is a key player in maintaining protein homeostasis. Proteins destined to be degraded by the UPS are tagged for destruction by conjugation to the small protein ubiquitin through the action of ubiquitin-conjugating (E2) and ubiquitin ligase (E3) enzymes, which can result in the assembly of ubiquitin chains on one or more lysine residues within the substrate. Proteins modified with an ubiquitin chain bind to ubiquitin receptors that link them to the 26S proteasome. The 26S proteasome is a large proteolytic complex that degrades ubiquitin-modified proteins and recycles the ubiquitin for future use. (Deshaies, Raymond J., Proteotoxic crisis, the ubiquitin-proteasome system, and cancer therapy. BMC Biology 201412:94; the content of which is incorporated herein by reference in its entirety).

The 20S proteasome is well characterized structurally (Tanaka, Keiji. "The Proteasome: Overview of Structure and Functions." Proceedings of the Japan Academy. Series B, Physical and Biological Sciences 85.1 (2009): 12-36. PMC. Web. 29 Sep. 2017; the content of which is incorporated herein by reference in its entirety). It is a well-organized protein complex with a sedimentation coefficient of 20S and a molecular mass of approximately 750 kDa. When viewed electron microscopically, the 20S proteasome appears as a cylinder-like structure in various eukaryotes, including yeast and mammals. It forms a packed particle, a result of axial stacking of two outer β-rings and two inner α-rings, which are made up of seven structurally similar α and β subunits, respectively; the rings form an $\alpha_{1-7}\beta_{1-7}\beta_{1-7}\alpha_{1-7}$ structure. The 20S proteasome plays essentially the same proteolytic roles in all eukaryotes, differing from proteasomes in prokaryotes that mainly consists of homo-hepatmeric α- and β-rings of the same α and β subunits, respectively, i.e., the αββα structure. (Proteasomes from structure to function: perspectives from Archaea. Maupin-Furlow J A, Humbard M A, Kirkland P A, Li W, Reuter C J, Wright A J, Zhou G Curr Top Dev Biol. 2006; 750:125-69.). The 20S proteasome processively degrades client proteins, generating oligopeptides ranging in length from 3 to 15 amino-acid residues. The resulting peptide products are subsequently hydrolyzed to amino acids by oligopeptidases and/or aminocarboxyl peptidases.

The enzymatically active proteasome is generally capped on either or both ends of the central 20S proteasomal core by regulatory proteins (RP). The RP recognizes client proteins marked by polyubiquitin chains, removes the chain and entraps the protein moiety, unfolds the substrate proteins, opens the α-ring, and transfers the unfolded substrates into the CP for destruction. The 19S RP comprises approximately 20 different subunits that can be subclassified into two groups: Regulatory particle of triple-ATPase (Rpt) subunits and Regulatory particle of non-ATPase (Rpn) subunits, both of which contain multiple proteins with molecular masses ranging from 10 to 110 kDa. The following is a brief description of the 19S RP, which comprises two sub-complexes: the lid and the base. (The regulatory particle of the *Saccharomyces cerevisiae* proteasome. Glickman M H, Rubin D M, Fried V A, Finley D Mol Cell Biol. 1998 June; 18(6):3149-62; the content of which is incorporated by reference in its entirety).

The catalytic core of the proteasome is a 20S cylinder, the inside of which contains two copies each of the active sites β1, β2, and β5. A second form of the proteasome, referred to as the immunoproteasome, is enriched in cells of the hematopoietic lineage and has a specialized function in immune cells, but an essentially analogous composition in which the β1, β2, and β5 sites are replaced by the closely related β1i, β2i, and β5i sites. The β5/β5i sites (also known as the chymotrypsin-like sites) are inhibited by bortezomib with high potency, whereas the β1 (caspase-like) sites have approximately 10-fold lower affinity and the β2 sites are not appreciably targeted under normal conditions. Substrates enter the 20S cylinder through its ends, which are capped with structures referred to as 19S regulatory particles (RPs). A 20S cylinder capped at each end with a 19S RP is referred to as the 26S proteasome. Assembly of the 26S proteasome is enabled by pockets at the ends of the 20S cylinder into which are inserted short carboxy-terminal tails that emanate from a heterohexameric ring of Rpt1-6 subunits in the 19S RP. Degradation substrates are tethered to the 26S proteasome via their ubiquitin chain, which binds to one or more of a set of receptor proteins, some of which (for example, Rpn10 and Rpn13) are intrinsic to the 19S RP, while others (for example, hRad23, hPLIC) shuttle on and off (Deshaies, Raymond J., Proteotoxic crisis, the ubiquitin-proteasome system, and cancer therapy. BMC Biology 201412:94; the content of which is incorporated by reference in its entirety).

Protein degradation by the proteasome can be ubiquitin dependent whereby a first ubiquitin binds to a protein targeted for degradation. Subsequently, more ubiquitin proteins bind to form a poly ubiquitin chain. Within the 19S cap, one or more ubiquitin receptors binds to the polyubiquitin chain and directed the ubiquitin tagged protein within the core of the proteasome for proteolysis.

In certain conditions, proteolytic activity and proteasome concentration are increased when the cell attempts to reduce the concentration of dysfunction, misfolded, or unnecessary proteins. For example, a cancer cell requires increased proteasome activity to prevent a toxic buildup of dysfunctional proteins within the cell as a result of the unregulated cellular function. Another example relates to oxidative stress whereby the proteasome activates NF-kB by separating NF-kB from IkB in response to TNFa or other external stress.

For example, cancer cells have a heightened dependence on mechanisms of protein homeostasis (proteostasis) including the UPS (Balch W E, Morimoto R I, Dillin A, Kelly J W: Adapting proteostasis for disease intervention. Science. 2008, 319: 916-919; the content of which is incorporated herein by reference in its entirety). Genome sequencing has revealed that cancer genomes are typically littered with dozens to hundreds of point mutations in protein coding sequences (Vogelstein B, Papadopoulos N, Velculescu V E, Zhou S, Diaz L A, Kinzler K W: Cancer genome landscapes. Science. 2013, 339: 1546-1558; the content of which is incorporated herein by reference in its entirety). Many of these mutated proteins are likely to present significant folding challenges, with increased degradation of the mutant protein via the UPS being one possible outcome. In addition, cancer cell genomes often contain large duplications, deletions, inversions, and translocations as well as altered copy numbers of entire chromosomes (aneuploidy). It has been estimated that over 90% of human solid tumors contain cells with more than two copies of one or more chromosomes (Weaver B A, Cleveland D W: Does aneuploidy cause cancer?. Curr Opin Cell Biol. 2006, 18: 658-667; the content of which is incorporated herein by reference in its entirety). These excess chromosomes continue to be expressed, and therefore protein synthesis in aneuploid cancer cells is often imbalanced, with proteins encoded by extra chromosomes being produced in excess over proteins encoded by chromosomes that are present in two copies (Williams B R, Prabhu V R, Hunter K E, Glazier C M, Whittaker C A, Housman D E, Amon A: Aneuploidy affects proliferation and spontaneous immortalization in mammalian cells. Science. 2008, 322: 703-709; the content of which is incorporated herein by reference in its entirety). This is particularly a problem for proteins that assemble to form stoichiometric complexes like the ribosome. In such cases, the excess proteins cannot attain stable conformations, and hence are degraded by the UPS (Warner J R, Mitra G, Schwindinger W F, Studeny M, Fried H M: Saccharomyces cerevisiae coordinates accumulation of yeast ribosomal proteins by modulating mRNA splicing, translational initiation, and protein turnover. Mol Cell Biol. 1985, 5: 1512-1521; the content of which is incorporated herein by reference in its entirety). Thus, this may create in cancer cells a heightened dependence on protein quality-control (PQC) mechanisms, including protein chaperones, the UPS, and autophagy (Williams B R, Amon A: Aneuploidy: cancer's fatal flaw?. Cancer Res. 2009, 69: 5289-5291; the content of which is incorporated herein by reference in its entirety).

The 26S proteasome is a multicatalytic proteinase complex with a highly ordered structure composed of 2 complexes, a 20S core and a 19S regulator. The 20S core is composed of 4 rings of 28 non-identical subunits; 2 rings are composed of 7 alpha subunits and 2 rings are composed of 7 beta subunits. The 19S regulator is composed of a base, which contains 6 ATPase subunits and 2 non-ATPase subunits, and a lid, which contains up to 10 non-ATPase subunits. Proteasomes are distributed throughout eukaryotic cells at a high concentration and cleave peptides in an ATP/ubiquitin-dependent process in a non-lysosomal pathway. An essential function of a modified proteasome, the immunoproteasome, is the processing of class I MHC peptides.

Psma2

Psma2 is a gene that encodes the proteasome subunit alpha type-2, a protein in humans which contributes to the complete assembly of the 20S proteasome complex. As an alpha subunit, Psma2 structurally promotes interaction between the 19s and 20s subunits. Such interaction is essential for general proteasome function. For example, the 19s subunit Psma6

Proteasome subunit alpha type-6 is a protein that in humans is encoded by the Psma6 gene. This protein is one of the 17 essential subunits (alpha subunits 1-7, constitutive beta subunits 1-7, and inducible subunits including beta1i, beta2i, beta5i) that contributes to the complete assembly of 20S proteasome complex.

Psma7

Proteasome subunit alpha type-7 also known as 20S proteasome subunit alpha-4 is a protein that in humans is encoded by the PSMA7 gene This protein is one of the 17 essential subunits (alpha subunits 1-7, constitutive beta subunits 1-7, and inducible subunits including beta1i, beta2i, beta5i) that contributes to the complete assembly of 20S proteasome complex.

Psmb4

A Proteasome subunit beta type-4a, also known as 20S proteasome subunit beta-7, is a protein that in humans is encoded by the PSMB4 gene. This protein is one of the 17 essential subunits (alpha subunits 1-7, constitutive beta subunits 1-7, and inducible subunits including beta1i, beta2i, beta5i) that contributes to the complete assembly of 20S proteasome complex. In particular, proteasome subunit beta type-2, along with other beta subunits, assembles into two heptameric rings and subsequently a proteolytic chamber for substrate degradation. The eukaryotic proteasome recognized degradable proteins, including damaged proteins for protein quality control purpose or key regulatory protein components for dynamic biological processes. An essential function of a modified proteasome, the immunoproteasome, is the processing of class I MHC peptides.

Psmb5

A Proteasome subunit beta type-5, also known as 20S proteasome subunit beta-5, is a protein that in humans is encoded by the Psmb5 gene. This protein is one of the 17 essential subunits (alpha subunits 1-7, constitutive beta subunits 1-7, and inducible subunits including beta1i, beta2i, beta5i) that contributes to the complete assembly of 20S proteasome complex. In particular, proteasome subunit beta type-5, along with other beta subunits, assembles into two heptameric rings and subsequently a proteolytic chamber for substrate degradation. This protein contains "chymotrypsin-like" activity and is capable of cleaving after large hydrophobic residues of peptide. The eukaryotic proteasome recognized degradable proteins, including damaged proteins for protein quality control purpose or key regulatory protein components for dynamic biological processes. An essential function of a modified proteasome, the immunoproteasome, is the processing of class I MHC peptides.

Psmc2

26S protease regulatory subunit 7, also known as 26S proteasome AAA-ATPase subunit Rpt1, is an enzyme that in humans is encoded by the PSMC2 gene. This protein is one of the 19 essential subunits of a complete assembled 19S proteasome complex. Six 26S proteasome AAA-ATPase subunits (Rpt1 (this protein), Rpt2, Rpt3, Rpt4, Rpt5, and Rpt6) together with four non-ATPase subunits (Rpn1, Rpn2, Rpn10, and Rpn13) form the base sub-complex of 19S regulatory particle for proteasome complex.

Psmc3

26S protease regulatory subunit 6A, also known as 26S proteasome AAA-ATPase subunit Rpt5, is an enzyme that in humans is encoded by the Psmc3 gene. This protein is one of the 19 essential subunits of a complete assembled 19S proteasome complex. Six 26S proteasome AAA-ATPase subunits (Rpt1, Rpt2, Rpt3, Rpt4, Rpt5 (i.e., Psmc3), and Rpt6) together with four non-ATPase subunits (Rpn1, Rpn2, Rpn10, and Rpn13) form the base sub complex of 19S regulatory particle for proteasome complex.

Psmc4

26S protease regulatory subunit 6B, also known as 26S proteasome AAA-ATPase subunit Rpt3, is an enzyme that in humans is encoded by the PSMC4 gene. This protein is one of the 19 essential subunits of a complete assembled 19S proteasome complex. Six 26S proteasome AAA-ATPase subunits (Rpt1, Rpt2, Rpt3 (i.e., Psmc4), Rpt4, Rpt5, and Rpt6) together with four non-ATPase subunits (Rpn1, Rpn2, Rpn10, and Rpn13) form the base sub complex of 19S regulatory particle for proteasome complex.

Psmc6

26S protease regulatory subunit S10B, also known as 26S proteasome AAA-ATPase subunit Rpt4, is an enzyme that in humans is encoded by the Psmc6 gene. This protein is one of the 19 essential subunits of a complete assembled 19S proteasome complex. Six 26S proteasome AAA-ATPase subunits (Rpt1, Rpt2, Rpt3, Rpt4 (Psmc6), Rpt5, and Rpt6) together with four non-ATPase subunits (Rpn1, Rpn2, Rpn10, and Rpn13) form the base sub-complex of 19S regulatory particle for proteasome complex.

Psmd1

26S proteasome non-ATPase regulatory subunit 1, also as known as 26S Proteasome Regulatory Subunit Rpn2, is a protein that in humans is encoded by the Psmd1 gene. This protein is one of the 19 essential subunits that contributes to the complete assembly of 19S proteasome complex.

Psmd3

26S proteasome non-ATPase regulatory subunit 3 is an enzyme that in humans is encoded by the Psmd3 gene.

Psmd4

26S proteasome non-ATPase regulatory subunit 4, also as known as 26S Proteasome Regulatory Subunit Rpn10(systematic nomenclature), is an enzyme that in humans is encoded by the PSMD4 gene. This protein is one of the 19 essential subunits that contributes to the complete assembly of 19S proteasome complex.

Psmd8

26S proteasome non-ATPase regulatory subunit 8 is an enzyme that in humans is encoded by the Psmd8 gene. This gene encodes a non-ATPase subunit of the 19S regulator. A pseudogene has been identified on chromosome 1.

Psmd9

26S proteasome non-ATPase regulatory subunit 9 is an enzyme that in humans is encoded by the PSMD9 gene. This gene encodes a non-ATPase subunit of the 19S regulator.

Psmd13

26S proteasome non-ATPase regulatory subunit 13 is an enzyme that in humans is encoded by the PSMD13 gene.

Psmd14

26S proteasome non-ATPase regulatory subunit 14, also known as 26S proteasome non-ATPase subunit Rpn11, is an enzyme that in humans is encoded by the Psmd14 gene. This protein is one of the 19 essential subunits of a complete assembled 19S proteasome complex. Nine subunits Rpn3, Rpn5, Rpn6, Rpn7, Rpn8, Rpn9, Rpn11, SEM1 (Yeast analogue for human protein DSS1), and Rpn12 form the lid sub complex of 19S regulatory particle for proteasome complex.

Psme4

Proteasome activator complex subunit 4 is a protein that in humans is encoded by the PSME4 gene.

Methods for Counteracting or Treating a Condition (e.g., a Human Subject Over a Certain Age) Aging Some embodiments disclosed herein provide methods for counteracting increase in gene expression (e.g., age-related increase or increase in a human subject that is over a certain age) or treating a disease (e.g., an age-related disease or a disease in a human subject that is over a certain age), comprising (optionally) identifying a human subject over the age of 35 and having an increased expression level of one or more genes associated with proteasome activity or an age-related disease; and administering to the human subject an effective amount of a nitroxide antioxidant. Healthy cells in a human subject over a certain age (e.g., 35 or 55) may have a natural decrease in proteasome activity. A disease or condition affecting an aging population may be associated with increased proteasome activity. In some embodiments, the methods comprise determining the expression level of one or more genes associated with proteasome activity. The identification step and/or the determination step may not be necessary in some instances, such as where an increased expression level of one or more genes associated with proteasome activity can be inferred from the human subject's age, family history, health conditions, medical history, habits, or a combination thereof. In some embodiments, the methods disclosed herein may be used to treat a human subject shows no symptoms of an age-related disease, but is at risk of having an age-related disease. Exemplary risk factors for an age-related disease include, but are not limited to, age, family history, health conditions, medical history, habits, or a combination thereof. In some embodiments, risk factors for an age-related disease comprise an increased expression level of one or more genes associated with proteasome activity.

In some embodiments, administering to the human subject an effective amount of the nitroxide antioxidant results in a decreased expression level of a gene, for example a gene associated with proteasome activity. The gene associated with proteasome activity can be Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The treatment of the human subject with the effective amount of the nitroxide antioxidant can result in a decreased expression level of the gene. For example, the treatment can result in decreased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof. The decreased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof, can increase the level of apoptosis based on the resulting cytotoxic protein buildup within the cell associated with the decreased expression levels. The increased level of apoptosis can result in a decrease in or disappearance of signs and symptoms of an age-related disease associated with increased proteasome activity, including the curing of the age-related disease. In some embodiments, the decreased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof, can increase the level of apoptosis. The increased level of apoptosis can result in a decrease in or disappearance of signs and symptoms of the age-related disease associated with increased proteasome activity, including the curing of the disease associated with age-related disease associated with increased proteasome activity.

In some embodiments, the levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof in the connective tissue, muscle tissue, nervous tissue, and/or epithelial tissue may change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Some embodiments disclosed herein provide methods for treating a disease related to aging in a human subject in need thereof, comprising (optionally) identifying a human subject over the age of 35 and having an age-related disease and having an increased expression level of a gene associated with proteasome activity; and administering to the human subject an effective amount of a nitroxide antioxidant. Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with proteasome activity is decreased.

Non-limiting examples of age-related diseases include cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension.

Methods for Decreasing Expression Level of a Gene

Some embodiments disclosed herein provide methods for decreasing the expression level of a gene in a human subject in need thereof, comprising (optionally) identifying a human subject having an increased expression level of a gene associated with proteasome activity; and administering to the human subject an effective amount of a nitroxide antioxidant. Some embodiments disclosed herein provide methods for treating a disease associated with an increased proteasome activity in a patient in need thereof, comprising (optionally) identifying a human subject having an increased expression level of a gene associated with proteasome activity; and administering to the human subject an effective amount of a nitroxide antioxidant. The increased expression level may be age-related, or disease related. In some embodiments, the disease may be cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension, or any combination thereof. Some embodiments disclosed herein provide methods for treating an individual in need thereof, comprising (optionally) identifying a human subject over the age of 35 in need of a decreased expression level of a gene associated with proteasome activity; and administering to the human subject an effective amount of a nitroxide antioxidant. In some embodiments, the methods comprise determining the expression level of one or more genes associated with proteasome activity. In some embodiments, the determination step comprises inferring increased expression level of one or more genes associated with proteasome activity based on the human subject's age, family history, health conditions, medical history, habits, or a combination thereof. In some embodiments, the methods disclosed herein may be used to treat a human subject shows no symptoms of a disease associated with increased proteasome activity, but is at risk of having a disease associated with increased proteasome activity. Exemplary risk factors for a disease associated with increased proteasome activity include, but are not limited to, age, family history, health conditions, medical history, habits, or a combination thereof.

In some embodiments, administering to the human subject an effective amount of the nitroxide antioxidant results in a decreased expression level of a gene, for example a gene associated with proteasome activity. The gene associated with proteasome activity can be Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The treatment of the human subject with the effective amount of the nitroxide antioxidant can result in a decreased expression level of the gene. For example, the treatment can decrease the expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof. The decreased expression of the gene can counteract the increase in the expression level of the gene.

Methods for Treating Cancer

Some embodiments disclosed herein provide methods for treating cancer in a human subject in need thereof, comprising (optionally) identifying a human subject having a cancer and in need of a decreased expression level of a gene associated with proteasome activity; and administering to the human subject an effective amount of a nitroxide antioxidant. In some embodiments, the methods disclosed herein may be used to treat a human subject that shows no symptoms of cancer, but is at risk of having cancer. Exemplary risk factors for cancer include, but are not limited to, age, family history, health conditions, medical history, habits, or a combination thereof. In some embodiments, risk factors for cancer comprise an increased expression level of one or more genes associated with proteasome activity. Anti-apoptotic upregulation of the proteasome complex (or a gene of the proteasome complex) and associated activity have been observed in cancer cells and accommodate increased production of misfolded proteins (Arlt, et al. Increased proteasome subunit protein expression and proteasome activity in colon cancer relate to an enhanced activation of nuclear factor E2-related factor 2 (Nrf2). Oncogene (2009) 28:3983-3996; Almond, et al. The proteasome: a novel target for cancer chemotherapy. Leukemia (2002) 16:433-443; Chen et al, Increased Proteasome Activity, Ubiquitin-Conjugating Enzymes, and eEF1A Translation Factor Detected in Breast Cancer Tissue. Molecular Biology, Pathobiology and Genetics. Cancer Research (2005) 65(13): 5599-5606; the content of each is incorporated herein by reference in its entirety).

Non-limiting examples of the methods for identifying a human subject having a cancer include colonoscopy; sigmoidoscopy; and high-sensitivity fecal occult blood tests. In some embodiments, methods for identifying a human subject having a cancer include low-dose helical computed tomography; mammography; and pap test and human papillomavirus (HPV) testing. In some embodiments, methods for identifying a human subject having a cancer include alpha-fetoprotein blood test; breast magnetic resonance imaging (MRI); CA-125 test; clinical breast exams and regular breast self-exams; prostate-specific antigen (PSA) testing; skin exams; transvaginal ultrasound; and virtual colonoscopy. In some embodiments, methods for identifying a human subject having a cancer include barium enema; biopsy; bone marrow aspiration and biopsy; bone scan; breast MRI for early detection of breast cancer; breast MRI; colonoscopy; computed tomography (CT) scan; digital rectal exam (DRE); blood and platelets testing; bone marrow testing; umbilical cord blood testing; electrocardiogram (EKG) and echocardiogram; endoscopic techniques; fecal occult blood tests; magnetic resonance imaging (MRI); mammography; multi gated acquisition (MUGA) scan; papanicolaou (pap) test; positron emission tomography and computed tomography (PET-CT) scan; sigmoidoscopy; tumor marker tests; ultrasound; upper endoscopy. In some embodiments, methods for identifying a human subject having a cancer include DNA sequencing; detecting presence of single nucleotide polymorphism (SNIP); and detecting the presence of certain protein markers.

In some embodiments, administering to the human subject an effective amount of the nitroxide antioxidant results in a decreased expression level of a gene, for example a gene associated with proteasome activity. The gene associated with proteasome activity can be Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The treatment of the human subject with the effective amount of the nitroxide antioxidant can result in a decreased expression of the gene. For example, the treatment can result in decreased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof. The decreased expression level of the gene can initiate apoptotic cascades resulting in programmed cell death. The increased level of apoptosis can result in a decrease in or disappearance of signs and symptoms of the cancer, including the curing of the cancer.

Non-limiting examples of cancer include bladder and other urothelial cancers; breast cancer; cervical cancer; colorectal cancer; endometrial cancer; endometrial cancer; esophageal cancer; liver (hepatocellular) cancer; lung cancer; neuroblastoma cancer; oral cavity and oropharyngeal cancer; ovarian, fallopian tube, and primary peritoneal cancer; prostate cancer; skin cancer; stomach (gastric) cancer; and testicular cancer.

Non-limiting examples of cancer include acute lymphoblastic leukemia, adult; acute myeloid leukemia, adult; adrenocortical carcinoma; aids-related lymphoma; anal cancer; bile duct cancer; bladder cancer; brain tumors, adult; breast cancer; breast cancer and pregnancy; breast cancer, male; carcinoid tumors, gastrointestinal; carcinoma of unknown primary; cervical cancer; chronic lymphocytic leukemia; chronic myelogenous leukemia; chronic myeloproliferative neoplasms; cns lymphoma, primary; colon cancer; endometrial cancer; esophageal cancer; extragonadal germ cell tumors; fallopian tube cancer; gallbladder cancer; gastric cancer; gastrointestinal carcinoid tumors; gastrointestinal stromal tumors; germ cell tumors, extragonadal; germ cell tumors, ovarian; gestational trophoblastic disease; hairy cell leukemia; hepatocellular (liver) cancer, adult primary; histiocytosis, langerhans cell; hodgkin lymphoma, adult; hypopharyngeal cancer; intraocular (eye) melanoma; islet cell tumors, pancreatic neuroendocrine tumors; kaposi sarcoma; kidney (renal cell) cancer; kidney (renal pelvis and ureter, transitional cell) cancer; langerhans cell histiocytosis; laryngeal cancer; leukemia, adult acute lymphoblastic; leukemia, adult acute myeloid; leukemia, chronic lymphocytic; leukemia, chronic myelogenous; leukemia, hairy cell; lip and oral cavity cancer; liver cancer, adult primary; lung cancer, non-small cell; lung cancer, small cell; lymphoma, adult Hodgkin; lymphoma, adult non-hodgkin; lymphoma, aids-related; lymphoma, primary cns; malignant mesothelioma; melanoma; melanoma, intraocular (eye); merkel cell carcinoma; metastatic squamous neck cancer with occult primary; multiple myeloma and other plasma cell neoplasms; mycosis fungoides and the sézary syndrome; myelodysplastic syndromes; myelodysplastic/myeloproliferative neoplasms; myeloproliferative neoplasms, chronic; paranasal sinus and nasal cavity cancer; nasopharyngeal cancer; neck cancer with occult primary, metastatic squamous; non-hodgkin lymphoma, adult; non-small cell lung cancer; oral cavity cancer, lip oropharyngeal cancer; ovarian epithelial cancer; ovarian germ cell tumors; ovarian low malignant potential tumors; pancreatic cancer; pancreatic neuroendocrine tumors (islet cell tumors); pheochromocytoma and paraganglioma; paranasal sinus and nasal cavity cancer; parathyroid cancer; penile cancer; pheochromocytoma and paraganglioma; pituitary tumors; plasma cell neoplasms, multiple myeloma and other; breast cancer and pregnancy; primary peritoneal cancer; prostate cancer; rectal cancer; renal cell cancer; transitional cell renal pelvis and ureter; salivary gland cancer; sarcoma, Kaposi; sarcoma, soft tissue, adult; sarcoma, uterine; mycosis fungoides and the sézary syndrome; skin cancer, melanoma; skin cancer, nonmelanoma; small cell lung cancer; small intestine cancer; stomach (gastric) cancer; testicular cancer; thymoma and thymic carcinoma; thyroid cancer; transitional cell cancer of the renal pelvis and ureter; trophoblastic disease, gestational; carcinoma of unknown primary; urethral cancer; uterine cancer, endometrial; uterine sarcoma; vaginal cancer; and vulvar cancer.

In some embodiments, non-limiting examples of cancer include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyPerproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Non-limiting examples of the cancer include acute lymphoblastic leukemia, childhood; acute myeloid leukemia/other myeloid malignancies, childhood; adrenocortical carcinoma, childhood; astrocytomas, childhood; atypical teratoid/rhabdoid tumor, childhood central nervous system; basal cell carcinoma, childhood; bladder cancer, childhood; bone, malignant fibrous histiocytoma of and osteosarcoma; brain and spinal cord tumors overview, childhood; brain stem glioma, childhood; (brain tumor), childhood astrocytomas; (brain tumor), childhood central nervous system atypical teratoid/rhabdoid tumor; (brain tumor), childhood central nervous system embryonal tumors; (brain tumor), childhood central nervous system germ cell tumors; (brain tumor), childhood craniopharyngioma; (brain tumor), childhood ependymoma; breast cancer, childhood; bronchial tumors, childhood; carcinoid tumors, childhood; carcinoma of unknown primary, childhood; cardiac (heart) tumors, childhood; central nervous system atypical teratoid/rhabdoid tumor, childhood; central nervous system embryonal tumors, childhood; central nervous system germ cell tumors, childhood; cervical cancer, childhood; chordoma, childhood; colorectal cancer, childhood; craniopharyngioma, childhood; effects, treatment for childhood cancer, late; embryonal tumors, central nervous system, childhood; ependymoma, childhood; esophageal tumors, childhood; esthesioneuroblastoma, childhood; ewing sarcoma; extracranial germ cell tumors, childhood; gastric (stomach) cancer, childhood; gastrointestinal stromal tumors, childhood; germ cell tumors, childhood central nervous system; germ cell tumors, childhood extracranial; glioma, childhood brain stem; head and neck cancer, childhood; heart tumors, childhood; hematopoietic cell transplantation, childhood; histiocytoma of bone, malignant fibrous and osteosarcoma; histiocytosis, langerhans cell; hodgkin lymphoma, childhood; kidney tumors of childhood, wilms tumor and other; langerhans cell histiocytosis; laryngeal cancer, childhood; late effects of treatment for childhood cancer; leukemia, childhood acute lymphoblastic; leukemia, childhood acute myeloid/other childhood myeloid malignancies; liver cancer, childhood; lung cancer, childhood; lymphoma, childhood Hodgkin; lymphoma, childhood non-Hodgkin; malignant fibrous histiocytoma of bone and osteosarcoma; melanoma, childhood; mesothelioma, childhood; midline tract carcinoma, childhood; multiple endocrine neoplasia, childhood; myeloid leukemia, childhood acute/other childhood myeloid malignancies; nasopharyngeal cancer, childhood; neuroblastoma, childhood; non-hodgkin lymphoma, childhood; oral cancer, childhood; osteosarcoma and malignant fibrous histiocytoma of bone; ovarian cancer, childhood; pancreatic cancer, childhood; papillomatosis, childhood; paraganglioma, childhood; pediatric supportive care; pheochromocytoma, childhood; pleuropulmonary blastoma, childhood; retinoblastoma; rhabdomyosarcoma, childhood; salivary gland cancer, childhood; sarcoma, childhood soft tissue; (sarcoma), ewing sarcoma; (sarcoma), osteosarcoma and malignant fibrous histiocytoma of bone; (sarcoma), childhood rhabdomyosarcoma; (sarcoma) childhood vascular tumors; skin cancer, childhood; spinal cord tumors overview, childhood brain and; squamous cell carcinoma (skin cancer), childhood; stomach (gastric) cancer, childhood; supportive care, pediatric; testicular cancer, childhood; thymoma and thymic carcinoma, childhood; thyroid tumors, childhood; transplantation, childhood hematopoietic; childhood carcinoma of unknown primary; unusual cancers of childhood; vaginal cancer, childhood; vascular tumors, childhood; and wilms tumor and other childhood kidney tumors.

Non-limiting examples of cancer include embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Methods for Treating Autoimmune Diseases

Some embodiments disclosed herein provide methods for treating an autoimmune disease in a human subject in need thereof, comprising (optionally) identifying a human subject having an autoimmune disease and in need of a decreased expression level of a gene associated with proteasome activity; and administering to the human subject an effective amount of a nitroxide antioxidant. In some embodiments, the nitroxide antioxidant can be, or act like, a proteasome inhibitor. A proteasome inhibitor can be a therapeutics of an autoimmune disease, such as rheumatoid arthritis, systemic lupus erythematosus, Sjögren's syndrome and sclerodema (Verbrugge et al. Proteasome inhibitors as experimental therapeutics of autoimmune diseases. Arthritis Res Ther. 2015; 17(1):1-10; the content of which is incorporated herein by reference in its entirety). In some embodiments, the methods disclosed herein may be used to treat a human subject shows no symptoms of an autoimmune disease, but is at risk of having an autoimmune disease. Exemplary risk factors for an autoimmune disease include, but are not limited to, age, family history, health conditions, medical history, habits, or a combination thereof. In some embodiments, risk factors for an autoimmune disease comprise an increased expression level of one or more genes associated with proteasome activity.

In some embodiments, Autoimmunity is the system of immune responses of an organism against its own healthy cells and tissues. Any disease that results from such an aberrant immune response is termed an "autoimmune disease". Prominent examples include celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), and dermatomyositis (DM). Autoimmune diseases are very often treated with steroids In some embodiments, administering to the human subject an effective amount of the nitroxide antioxidant results in a decreased expression level of a gene, for example a gene associated with proteasome activity. The gene associated with proteasome activity can be Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The treatment of the human subject with the effective amount of the nitroxide antioxidant can result in a decreased expression level of the gene. For example, the treatment can result in decreased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof. The increased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof, can increase the level of apoptosis. The increased level of apoptosis can result in a decrease in or disappearance of signs and symptoms of the autoimmune disease, including the curing of the autoimmune disease. In some embodiments, the decreased expression levels of Psma6, Psmd3, Psmb4, Psmb5, Psmc6, Psme4, Psmd9, Psmd12, Psmd14, Psmd4, Psma2, Psmc2, Psmc3, Psmd13, Psma7, Psmc4, or any combination thereof, can increase the level of apoptosis. The increased level of apoptosis can result in a decrease in or disappearance of signs and symptoms of the autoimmune disease, including the curing of the autoimmune disease.

Non-limiting examples of autoimmune diseases include rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GB S) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the present application can be used to treat humans suffering from autoimmune diseases, in particular those associated with inflammation, including, rheumatoid spondylitis, allergy, autoimmune diabetes, autoimmune uveitis.

Non-limiting examples of autoimmune diseases include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, Mycobacterium avium intracellulare, Mycobacterium tuberculosis, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, Pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis *nigricans*, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

Nitroxide Antioxidant

Non-limiting examples of the nitroxide antioxidant include 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Amin omethyl-PROXYL, 3-Cyano-PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-phosphonooxy, and the like.

The use of other nitroxide compounds is also contemplated. According to certain embodiments the nitroxide compound can be selected from the following formulas:

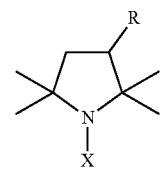

wherein X is selected from O— and OH, and R is selected from COOH, CONH, CN, and CH2NH2;

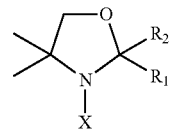

wherein X is selected from O— and OH, and R1 is selected from CH3 and spirocyclohexyl, and R2 is selected from C2H5 and spirocyclohexyl;

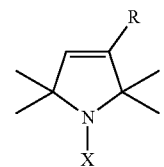

wherein X is selected from O— and OH and R is selected from CONH; and

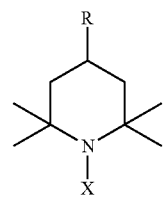

wherein X is selected from O— and OH and R is selected from H, OH, and NH2.

Suitable nitroxide compounds can also be found in Proctor, U.S. Pat. No. 5,352,442, and Mitchell et al., U.S. Pat. No. 5,462,946, both of which are hereby incorporated by reference in their entireties.

In some embodiments, the nitroxide antioxidant includes or is associated with (e.g., binds to or is conjugated with) a bioeffector molecule. For example, the bioeffector molecule is a targeting subunit bound to the nitroxide antioxidant, such as a mitochondrial targeting subunit. A targeting subunit can direct activity of the nitroxide antioxidant to a predetermined location within or on the cell. Non-limiting examples of mitochondrial targeting bioeffector molecules includes triphenylphosphine (TPP), gramicidin, and any functional group effectively charged to be attracted to the polarized mitochondria.

In some embodiments, the nitroxide antioxidant is structurally cyclic having a ring structure including a nitroxide molecule incorporated therein. In some embodiments, the nitroxide antioxidant is characterized as the nitroxide molecule functioning as the catalytic center.

Dosage

In some embodiments, the nitroxide antioxidant, non-toxic salts thereof, acid addition salts thereof or hydrates thereof may be administered systemically or locally, usually by oral or parenteral administration. The doses to be administered can be determined depending upon, for example, age, body weight, symptom, the desired therapeutic effect, the route of administration, and the duration of the treatment. In the human adult, the dose per person at a time can be generally from about 0.01 to about 1000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time can be generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration can also contemplated for from 1 to 24 hours per day to achieve a target concentration from about 0.01 mg/L to about 100 mg/L. Non-limiting examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does can depend upon various conditions, and there may be cases wherein doses lower than or greater than the ranges specified above are used.

Compositions

The nitroxide antioxidant can be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the nitroxide antioxidant is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. For injections, the nitroxide antioxidant can be dissolved, suspended and emulsified in a solvent. The solvents include, for example, distilled water for injection, physiological salt solution, vegetable oil, propylene glycol, polyethylene glycol, alcohol such as ethanol, or a mixture thereof. Moreover the injections can also include stabilizing agents, agents to assist dissolution (e.g. glutamic acid, aspartic acid or POLYSORBATE80™), suspending agents, emulsifying agents, soothing agents, buffer agents, preserving agents, etc. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise the nixtroxide antioxidant and are administered by methods known in the art.

Spray compositions can comprise additional substances other than diluents: e.g. stabilizing agents (e.g. sodium sulfite hydride), isotonic buffers (e.g. sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol. The minimum quantity of suspending agent can be approximately 0.1 to 0.2 percent by weight of the total composition. The amount of suspending agent can be less than about 4 percent by weight of the total composition to maintain an upper particle size limit of less than 10 microns or 5 microns. Propellants that may be employed include hydrofluoroalkane propellants and chlorofluorocarbon propellants. Dry powder inhalation may also be employed.

EXAMPLES

Some aspects of the embodiments discussed above are disclosed in further detail in the following examples, which are not in any way intended to limit the scope of the present disclosure.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1. Effects of Tempol on Expression of Genes Associated with Proteasome Activity To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in the cardiac tissue was assessed using chip-based microarray technology. Such chips are well known in the art and are widely used to assess gene expression. The experimental results showed that five genes associated with proteasome activity, Psma6, Psmd3, Psmb4, Psmb5, Psmc6, Psme4, Psmd9, Psmd12, Psmd14, Psmd4, Psma2, Psmc2, Psmc3, Psmd13, Psma7, and Psmc4, exhibited statistically significant decrease in expression. This result is shown in Table 1.

TABLE 1

Genes Associated With Proteasome Activity Exhibiting Decreased Expression In White Adipose Tissue After Tempol Administration

| Symbol | Gene title | Control mice | Tempol-treated mice | Fold change | P-value |
|---|---|---|---|---|---|
| Psma6 | Alpha type subunit 6 | 3782 | 3467 | −1.09 | 0.04 |
| Psmd3 | Non-ATPase 26s subunit 3 | 1146 | 1017 | −1.12 | 0.03 |
| Psmb4 | Beta type subunit 4 | 3622 | 3614 | −1.15 | 0.02 |
| Psmb5 | Best type subunit 5 | 2018 | 1754 | −1.15 | 0.01 |
| Psmc6 | ATPase 26s subunit 6 | 1686 | 1449 | −1.16 | 0.03 |
| Psme4 | Activator subunit 4 | 1257 | 1086 | −1.16 | 0.03 |
| Psmd9 | Non-ATPase 26s subunit 9 | 364 | 310 | −1.18 | 0.01 |
| Psmd12 | Non-ATPase 26s subunit 12 | 1326 | 1098 | −1.20 | 0.00 |
| Psmd14 | Non-ATPase 26s subunit 14 | 3294 | 2745 | −1.20 | 0.00 |
| Psmd4 | Non-ATPase 26s subunit 4 | 3133 | 2610 | −1.20 | 0.04 |
| Psma2 | Alpha type subunit 2 | 3744 | 3123 | −1.20 | 0.00 |
| Psmc2 | ATPase 26s subunit 2 | 2689 | 2176 | −1.23 | 0.01 |
| Psmc3 | ATPase 26s subunit 3 | 2235 | 1810 | −1.23 | 0.00 |
| Psmd13 | Non-ATPase 26s subunit 13 | 1294 | 1047 | −1.23 | 0.01 |
| Psma7 | Alpha type subunit 7 | 1864 | 1513 | −1.23 | 0.00 |
| Psmc4 | ATPase 26s subunit 4 | 1673 | 1101 | −1.52 | 0.02 |

Example 2. Treating Age-Related Increase in Gene Expression

A 70-kilogram human subject over the age of 65 is identified as having, or known to have, or suspected of having increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4, is decreased.

Example 3. Treating a Human Subject with Increased Gene Expression

A 70-kilogram human subject is identified as having, or known to have, or suspected of having increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4, is decreased.

Example 4. Treating a Human Subject with an Age-Related Disease

A 70-kilogram human subject over the age of 65 and having a cardiovascular disease is identified for increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. Or a 70-kilogram human subject over the age of 65 is known to have a cardiovascular disease and/or increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4, is decreased.

Example 5. Treating a Human Subject at Risk of Developing Cancer

A 70-kilogram human subject at risk of developing colorectal cancer is identified for increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. Or a 70-kilogram human subject is known to be at risk of developing colorectal cancer and/or have increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4, is decreased.

Example 6. Treating a Human Subject at Risk of Developing an Autoimmune Disease

A 70-kilogram human subject at risk of developing an autoimmune disease (e.g., rheumatoid arthritis) is identified for increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. Or a 70-kilogram human subject is known to be at risk of developing an autoimmune disease and/or have increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4, is decreased.

Example 7. Treating a Human Subject at Risk of Developing a Condition Due to Aging A 70-kilogram human subject of 45 years old at risk of developing a condition due to aging is identified. Or a 70-kilogram human subject of 45 years old is known to be at risk of developing a condition. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4, is decreased.

Example 8. Treating a Human Subject at Risk of Developing a Neruodegenerative Disease A 70-kilogram human subject at risk of developing a neurodegenerative disease (e.g., Parkinson's Disease) is identified for increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. Or a 70-kilogram human subject is known to be at risk of developing a neurodegenerative disease and/or have increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4, is decreased.

Example 9. Treating a Human Subject Having an Infection

A 70-kilogram human subject having an infection (e.g., a bacterial, fungal, or viral infection) is identified for increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. Or a 70-kilogram human subject is known to have an infection and/or have increased expression level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Psma6, Psmd3, Psmb4, Psmb5, Psmc6, Psme4, Psmd9, Psmd12, Psmd14, Psmd4, Psma2, Psmc2, Psmc3, Psmd13, Psma7, or Psmc4, is decreased.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for decreasing the expression level of Psma6 in a human subject, the method comprising:
   identifying the human subject both having an increased expression level of Psma6 and having a disease associated with the increased expression level Psma6; and
   administering an effective amount of a nitroxide antioxidant to the human subject,
   the nitroxide antioxidant selected from the group consisting of 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Aminomethyl-PROXYL, 3-Cyano-PROXYL, 3-Carbamoyl-PROXYL, 3-Carboxy-PROXYL, and 4-Oxo-TEMPO,
   whereby the expression level of Psma6 is decreased,
   wherein the disease associated with the increased expression level of Psma6 is atherosclerosis, and
   wherein identifying the human subject having an increased expression level of Psma6 comprises measuring the expression level of Psma6 in the human subject.

2. The method of claim 1, wherein the nitroxide antioxidant is TEMPOL.

3. The method of claim 1, wherein the nitroxide antioxidant is OXANO.

4. The method of claim 1, wherein the nitroxide antioxidant is TEMPO.

5. The method of claim 1, wherein the nitroxide antioxidant is Tempamine.

6. The method of claim 1, wherein the nitroxide antioxidant is 3-Aminomethyl-PROXYL.

7. The method of claim 1, wherein the nitroxide antioxidant is 3-Cyano-PROXYL.

8. The method of claim 1, wherein the nitroxide antioxidant is 3-Carbamoyl-PROXYL.

9. The method of claim 1, wherein the nitroxide antioxidant is 3-Carboxy-PROXYL.

10. The method of claim 1, wherein the nitroxide antioxidant is 4-Oxo-TEMPO.

* * * * *